United States Patent [19]

Tao

[11] 4,233,038
[45] Nov. 11, 1980

[54] REACTIVATION SYSTEM FOR WATER-CARBON DIOXIDE ADSORBERS

[75] Inventor: John C. Tao, Allentown, Pa.

[73] Assignee: Air Products and Chemicals, Inc., Allentown, Pa.

[21] Appl. No.: 64,233

[22] Filed: Aug. 6, 1979

[51] Int. Cl.³ .................. B01D 53/04; B01D 53/26
[52] U.S. Cl. ................................. 55/33; 55/62; 55/68; 55/75
[58] Field of Search .......... 55/25, 26, 31, 33, 58, 55/62, 68, 74, 75

[56] References Cited

U.S. PATENT DOCUMENTS

| | | | |
|---|---|---|---|
| 3,109,722 | 11/1963 | Dow | 55/33 X |
| 3,150,942 | 9/1964 | Vasan | 55/33 X |
| 3,323,288 | 6/1967 | Cheung et al. | 55/62 X |
| 3,365,859 | 1/1968 | Sandberg | 55/62 X |
| 3,436,839 | 4/1969 | Ellington | 55/33 X |
| 3,594,983 | 7/1971 | Yearout | 55/33 |
| 3,710,547 | 1/1973 | Nelson | 55/62 X |
| 3,720,042 | 3/1973 | Simonet | 55/62 X |
| 3,738,084 | 6/1973 | Simonet et al. | 55/62 X |
| 3,841,058 | 10/1974 | Templeman | 55/33 |
| 4,144,038 | 3/1979 | Armond | 55/58 |

FOREIGN PATENT DOCUMENTS 2005910 12/1969 France ................... 55/33

Primary Examiner—Robert H. Spitzer
Attorney, Agent, or Firm—William F. Marsh; E. Eugene Innis

[57] ABSTRACT

A cyclic process for the separation of water and carbon dioxide contaminants from a feed gas stream by adsorption on molecular sieve adsorbents and the subsequent regeneration of the adsorbents is disclosed. Adsorption of the water and $CO_2$ contaminants is accomplished by passing the feed gas stream through first and second adsorbent zones, containing molecular sieve adsorbents. Water is adsorbed in the first zone and the carbon dioxide is adsorbed primarily in the second zone. Regeneration of the adsorbent zones is accomplished by the sequential steps of:

(1) introducing a heated regeneration gas intemediate the first and second adsorbent zone and passing the heated regeneration gas through the first adsorbent zone in a countercurrent direction until the regeneration gas exiting the first adsorbent zone reaches approximately 250° F. to 350° F.;

(2) discontinuing the introduction of the heated regeneration gas and introducing cool regeneration gas at the feed gas inlet through the first adsorbent zone and passing the cool regeneration gas sequentially through the first and second adsorbent zones, thereby pushing a thermal pulse through the second zone and continuing the flow of cool regeneration gas until the first and second zones are cooled to the adsorption operating temperature.

7 Claims, 5 Drawing Figures

REACTIVATION SYSTEM FOR WATER-CARBON DIOXIDE ADSORBERS

BACKGROUND OF THE INVENTION

1. Field of the Invention

This invention relates to a cyclic process for the removal of carbon dioxide and water contaminants from a feed gas stream by adsorption on molecular sieve adsorbents. More particularly, the invention relates to an improved method for the regeneration of the adsorbents. Removal of water and carbon dioxide contaminants from feed gas streams is often necessary prior to further processing for the feed gas stream. Examples of such further processing requiring removal of water and carbon dioxide contaminants is the cryogenic distillation of air, the purification of hydrogen gas streams, hydrogen and carbon monoxide streams, or the cryogenic liquefaction of natural gas feed streams to produce liquefied natural gas (LNG).

2. The Prior Art

Crystalline zeolites, commonly referred to as molecular sieves, have been used for the adsorption of water and/or carbon dioxide from feed gas streams in the past. Various processes involving the adsorption and regeneration phases for such molecular sieves have been used. Because of the great affinity of the molecular sieves for water and carbon dioxide molecules which makes possible their removal from feed gas streams to very low concentrations, substantial time and energy must be expended in the regeneration of the molecular sieves after they have reached saturation during the adsorption phase. The heat, time and energy required to regenerate the molecular sieves in the adsorbent beds thus determined to a large extent the size of the equipment and the total energy requirements. As a consequence, considerable effort has been devoted in the past to the development of efficient regeneration methods.

Various methods have been employed for the regeneration of the adsorbent to effect the desorption of the impurities. These methods have included the depressurization, heating, and the elution of the adsorbent beds and combinations of the three. Because of the strong affinity of the molecular sieve adsorbents for carbon dioxide and water impurities and the high adsorptive capacity, the most commonly employed regeneration process has involved depressurization of the adsorbent beds, the heating of the beds to elevated temperatures and the purging of the adsorbent beds with the regeneration gas so that it is at least partially freed of the impurities. Often the adsorbent beds are heated by means of the regeneration gas itself, the regeneration gas having first been heated before introduction to the adsorbent beds. Due to the large adsorbent and pressure vessel masses which must be heated and subsequently cooled in commercial scale facilities, substantial amounts of energy are expended for both heating and cooling and, consequently, cycle times required to achieve the requisite heat transfer are correspondingly long.

It has been recognized that due to the relative affinities and capacities of molecular sieves for water and carbon dioxide, that the water is preferentially adsorbed in a first adsorbent zone proximate the introduction point of the feed gas stream to the molecular sieve adsorbent. The carbon dioxide is secondarily adsorbed by the molecular sieve in a second adsorbent zone downstream from the water zone. Because of the greater affinity of the molecular sieve for water than carbon dioxide, more severe regeneration conditions are required to desorb the water than the carbon dioxide. This generally involves a higher regeneration temperature.

In order to reduce the heating and cooling requirements and the quantities of purified regeneration gas, and to shorten the cycle times, various methods have been devised for regenerating the carbon dioxide and water zones under differentiated conditions. For example, see U.S. Pat. Nos. 3,150,942; 3,710,547; 3,738,084; and 3,841,058. French Pat. No. 2.005.910, also discloses method and apparatus for the adsorption of water and carbon dioxide from gas mixtures and a method for the regeneration of the molecular sieves used for the adsorption.

Accordingly, it is an object of this invention to provide an improved process for the adsorption of water and carbon dioxide contaminants from a feed gas stream by adsorption on molecular sieve adsorbents and subsequent regeneration of the adsorbent. It is further an object of the invention to provide an improved process that consumes less energy for the heating and cooling cycles during adsorbent bed regeneration.

It is still another object of the invention to reduce the regeneration cycle time in consequence of the reduced heating and cooling requirements and to correspondingly reduce the adsorbent bed volumes and to reduce the operating and capital costs of the process and apparatus.

SUMMARY OF THE INVENTION

These and other objects of the invention are obtained in a cyclic process for the separation of water and carbon dioxide contaminents from a feed gas stream by adsorption on molecular sieve adsorbents and the subsequent regeneration of the adsorbents. The feed gas stream is passed sequentially through first and second adsorbent zones wherein substantially all of the water is adsorbed in the first adsorbent zone and carbon dioxide is adsorbed in the second adsorbent zone. The flow of the feed gas stream through the adsorbent zones is then discontinued and the adsorbent is regenerated by an improved method. The improved method comprises regenerating the adsorbent zones in two stages. In the first stage, a heated stream of purified regeneration gas is introduced intermediate the first and second adsorbent zones and is passed through the first, or water, adsorbent zone in a countercurrent direction. When the temperature of the regeneration gas stream exiting the water adsorbent zone rises to a point approaching that of the hot regeneration gas stream introduced, the flow of the hot regeneration gas is discontinued. The second step comprises the introduction of a cool purified regeneration gas stream at the feed gas stream inlet end of the first zone and passing the cool regeneration gas through the first zone and sequentially through the second, or carbon dioxide, adsorption zone until the heat contained in the first adsorbent zone has been "pushed" out of the first zone and through the second zone, thereby simultaneously cooling the first zone and using the thermal pulse to regenerate the carbon dioxide adsorbent zone.

According to a preferred embodiment, the heated regeneration gas introduced intermediate the first and second adsorbent zones is at an initial temperature of approximately 450° F. to 700° F. The introduction of the heated regeneration gas is discontinued when the regeneration gas exiting from the first adsorbent zone reaches a temperature of approximately 250° to 350° F.

The cool regeneration gas introduced at the feed gas inlet end of the first adsorbent bed is preferably cooled to approximately 40° F. However, depending upon the availability of various temperature streams and the conditions under which adsorption is carried out, the temperature of the cool regeneration gas stream may be as high as 130° F.

This invention is particularly applicable, though not necessarily limited, to feed gas streams in which the major component from which the water and carbon dioxide contaminants are to be separated is air, hydrogen, or methane.

Throughout the specification and claims, reference to "counterflow" or "countercurrent" is intended to connote a flow direction through the adsorbent bed or zones in a direction opposite to the normal feed gas flow therethrough during the adsorption cycle. "Cocurrent" refers to a flow passing through the adsorber beds in the same direction as the feed gas flows therethrough.

BRIEF DESCRIPTION OF THE DRAWING

The practice of the invention and its objects will more readily be understood from the DETAILED DESCRIPTION and the accompanying drawings.

DESCRIPTION OF THE INVENTION

The invention and the preferred embodiments thereof will be described with reference to the drawings.

Figure 1:
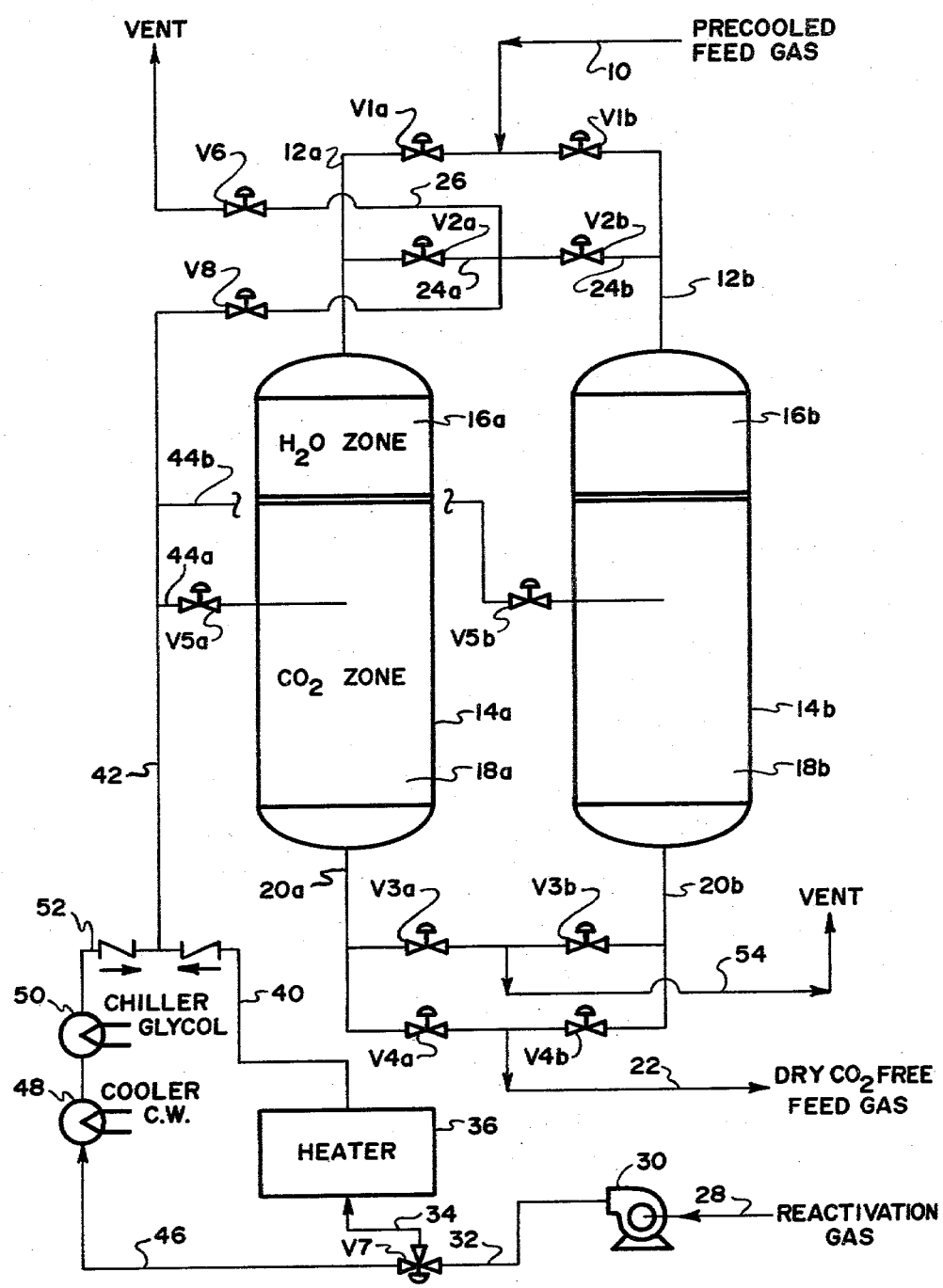
FIG. 1 is a schematic representation of apparatus for practicing the invention showing a preferred embodiment using two parallel adsorber vessels.

FIG. 1 shows a schematic flow diagram for the preferred embodiment of the invention utilizing two parallel adsorber vessels for removal of water and carbon dioxide contaminants from a feed gas stream. The precooled and phase separated feed gas enters through line 10. This feed gas contains water and carbon dioxide contaminants. The main component of the feed gas may be a mixture of gases which are to be subsequently separated by cryogenic separation such as air or light hydrocarbons. Alternatively, the main component may be a single component such as hydrogen from which water and carbon dioxide contaminants are to be removed.

In the preferred embodiment of the invention two adsorber vessels are provided, each of which contains zeolite molecular sieve adsorbents in two zones. These zones may comprise physically separated adsorbent beds within the vessel or may comprise a single continuous adsorbent bed, the boundry between the first and second adsorbent zones being defined by a heated regeneration gas nozzle and distributor being disposed at a point along the length of the bed. Sizing and design of the adsorbent vessels and zones is well within the skill of the art once the process and concept of this invention is generally understood. Alternatively, the two adsorbent zones may be contained in separate vessels connected in series.

In the preferred embodiment for adsorption of water and $CO_2$ from a feed gas stream comprising air, the molecular sieve in both the water and $CO_2$ adsorption zones is Linde Type 13X molecular sieve. The water adsorption zone may also comprise an initial portion of a non-molecular sieve adsorbent such as silica gel.

The operation of Applicant's invention will now be described in the context of adsorption vessel 14a being in the adsorption cycle and vessel 14b being in the regeneration cycle.

A feed gas stream containing water and carbon dioxide contaminants which are to be removed enters adsorption vessel 14a through line 10, open valve V1a, and line 12a. This feed gas stream has been previously cooled and separated from entrained water and particulate material. The feed gas then passes through a first adsorbent zone, or bed, 16a containing molecular sieve adsorbent. This bed may also contain a top layer of adsorbent such as alumina or silica gel for initial feed gas distribution and water adsorption from the saturated feed gas. In this first adsorbent zone, the water is adsorbed from the feed gas stream.

Figure 2:
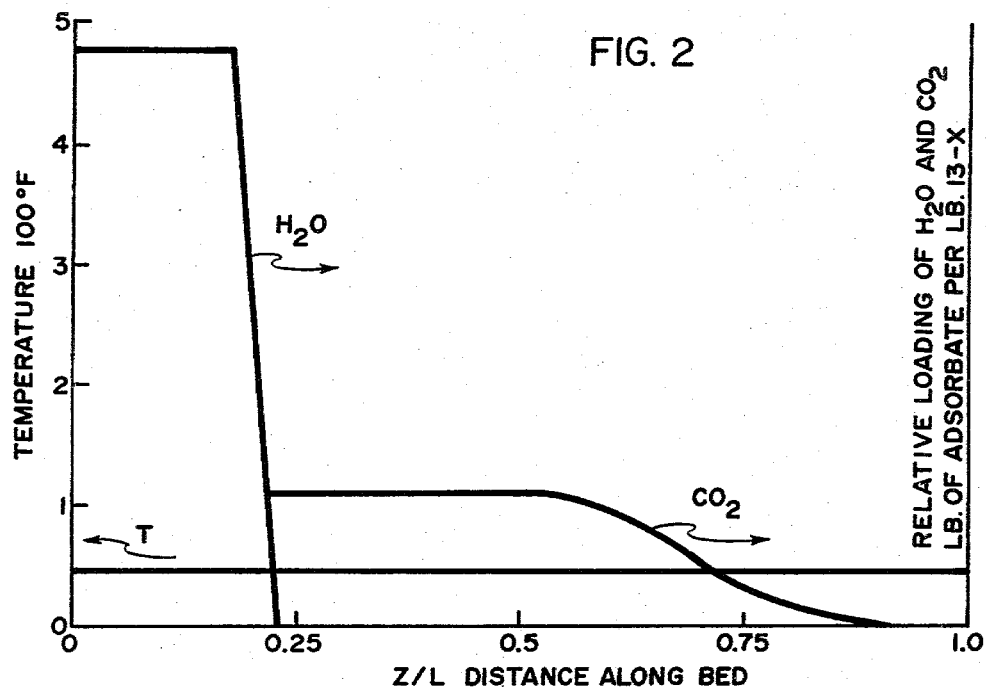
FIGS. 2 through 5 are diagrams showing the dimensionless measure of the relative loading of water and carbon dioxide contaminants on the adsorbents and the relative temperature profiles as a function of the dimensionless adsorber bed length at various times during the regeneration cycle.

The feed gas stream then passes through a second adsorbent zone 18a containing molecular sieve wherein the carbon dioxide is adsorbed from the feed gas stream. The feed gas stream exiting from the second adsorbent zone is substantially free of both water and carbon dioxide and leaves adsorber vessel 14a through line 20a, through open valve V4a, and line 22 through which the substantially water and carbon dioxide-free feed gas is conducted to the subsequent processing steps. The adsorption phase continues in vessel 14a until the water and carbon dioxide adsorption zones approach saturation as in conventional operations. The relative water and carbon dioxide leading and the bed temperature profile are as shown in FIG. 2.

The regeneration of the adsorbent in vessel 14b according to the present invention proceeds as follows.

Figure 3:
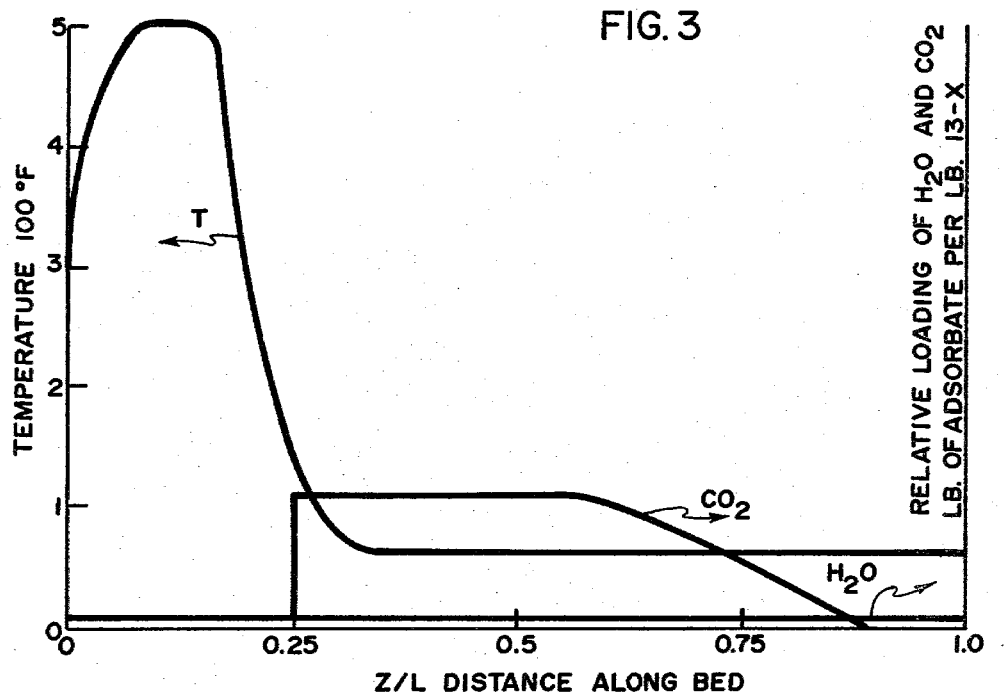

After the flow of feed gas stream through vessel 14b has been discontinued upon saturation of the adsorbent beds with water and carbon dioxide, valves V1b and V4b are closed. Valve V2b is opened and the pressure in adsorber vessel 14b is reduced from 105 psia to 28 psia over a 15 minute period through line 12b, open valve V2b, in line 24b and then through line 26 open valve V6 to a vent. Upon depressurization of vessel 14b, water and $CO_2$ free reactivation gas, generally comprising the purified main component of the feed gas stream such as nitrogen when the feed air stream is air, is brought through line 28, compressed in compressor 30 to a suitable pressure for regeneration, in this case approximately 30 psia, and conducted through line 32, three way valve V7 to line 34 and a heater 36 wherein its temperature is raised to approximately 450° F. to 700° F. The heated regeneration gas is then conducted through lines 40, 42, 44b and open valve V5b and introduced into the adsorbent vessel 14b at a point intermediate the first and second adsorbent zones. During the introduction of the heated regeneration gas, valves V3a, V3b, and V4a, and V4b are closed and valve V2b and V6 remain open. The heated regeneration gas passes through the first adsorbent zone in a countercurrent direction and exits vessel 14b through line 12b, line 24b and valve V2b, then through line 26 and open valve V6 to a vent. The flow of heated regeneration gas is continued until the water adsorption zone has been heated and the temperature of the regeneration gas leaving the first adsorbent zone is approximately 250° F. to 350° F. At the end of the heating cycle the temperature and relative loading concentrations of the carbon dioxide and water contaminants along the length of the adsorber zones are as shown in FIG. 3. A high temperature wave has been established in the first adsorption zone and the loading of water and $CO_2$ contaminants on the adsorbent have been reduced to extremely low levels in the first adsorbent zone. The concentration of carbon dioxide in the second adsorbent zone remains substantially the same as immediately prior to the beginning of the regeneration in the second adsorbent zone.

Figure 4:
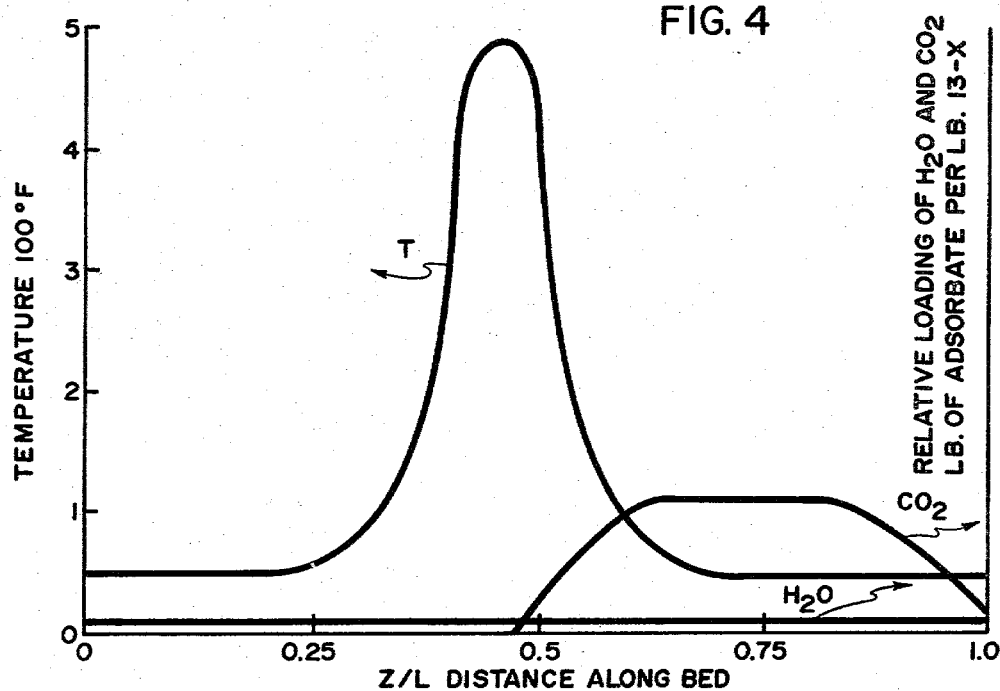
Figure 5:
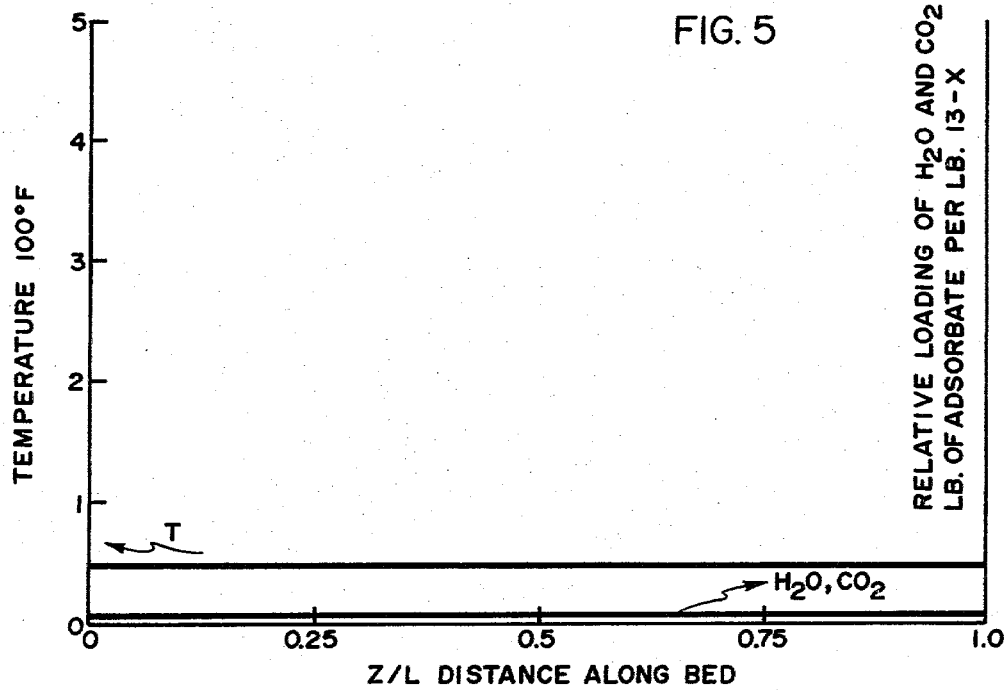

When the temperature of the regeneration gas exiting the first adsorption zone reaches approximately 250° F. to 350° F., heater 36 is turned off, valve V7 is operated to direct the flow of the regeneration gas from the compressor through line 32 thence through line 46 cooler 48 and chiller 50, line 52, and thence through line 42. Valve V5b and valve V6 are closed and valve V8 is opened to allow the introduction of the cooled regeneration gas to the feed gas inlet end of adsorber vessel 14b. Valve V3b is opened. The cooled regeneration gas at a temperature of approximately 40° F. to 70° F. is then passed through the first adsorbent bed and then through the second adsorbent bed in a cocurrent direction, that is, in the same direction as the feed gas stream during the adsorption phase. The cooled regeneration gas passing through the adsorber vessel exits through lines 20b, valve V3b and vent line 54. During this time, the cool regeneration gas cools the first adsorbent zone which is substantially free of water and $CO_2$. The regeneration gas picks up the heat from the first adsorbent bed and carries it into the second adsorbent bed, thus in effect pushing a "thermal pulse" or "thermal wave" from the inlet end of vessel 14b through the second adsorbent bed and out the outlet end of adsorbent vessel 14b, as represented in FIG. 4. This thermal wave serves to desorb the $CO_2$ from the molecular sieve adsorbent in the second adsorbent zone. Thus, the first adsorbent zone is simultaneously cooled with the regeneration of the second or carbon dioxide adsorbent zone. The thermal pulse passing through the second adsorbent zone will raise the temperature of the adsorbent to between 200° F. and 350° F. which is required for desorption of the carbon dioxide. Upon passage of the thermal pulse out of the outlet of vessel 14b, both absorbent beds have been thoroughly regenerated to low residual levels of adsorbed water and carbon dioxide and both beds have been cooled to approximately 40° F. in preparation for the next adsorption phase, the final temperature profile and relative water and carbon dioxide loadings being represented in FIG. 5.

Valves V2b, V3b are closed and valves V1b and V4b are opened to place vessel 14b in the adsorption mode.

As an example of a preferred embodiment in the adsorption of water and carbon dioxide from an air stream entering at 40° F. then 105 psia and a flow rate of 2,000 pound moles per hour saturated with water at 52.2 pounds of water per hour and a carbon dioxide concentration of 350 parts per million by volume, the following data is presented for a typical process design. The type of molecular sieve adsorbent chosen is Linde Type 13×molecular sieve. Seventy-five hundred pounds of molecular sieve is used in the adsorber vessel with approximately 1,875 pounds of molecular sieve located above the heated regeneration gas nozzle and comprising the first adsorbent bed. The remainder, or 5,525 pounds of molecular sieve, lies between the heater regeneration gas inlet nozzle and the outlet of the adsorber vessel and comprises the second, or carbon dioxide adsorbent bed. These volumes include approximately a 65% safety factor in sizing the beds for a four hour adsorption phase cycle. After the adsorption phase is terminated, the adsorber vessel is depressurized over a 15-minute period from the pressure of 105 psia to a regeneration pressure of 28 psia. The reactivation nitrogen is heated to between 550° to 600° F. and is introduced intermediate the first and second adsorbent zones at a flow rate of 4,000 pounds per hour of dry, $CO_2$-free nitrogen. This regeneration gas heats the first adsorbent bed until the outlet temperature of the regeneration gas from the bed reaches approximately 300° F. This requires approximately 35 minutes and a total heat load of about one million Btu/hr. In the cooling cycle, 4,000 lbs. per hour of dry, $CO_2$-free waste nitrogen is chilled to 40° F. and passed through the first and second adsorbent zones in a cocurrent direction. The cooling phase flow of nitrogen is continued for a period of approximately 2 hours, during which time the thermal pulse is pushed through the second adsorbent bed. The maximum temperature of the thermal pulse passing through the second $CO_2$ adsorption bed is approximately 500° F. at the inlet to the second adsorbent bed and approximately 200° F. at the end of the cooling cycle. The total regeneration cycle is approximately four hours to correspond to the adsorption phase cycle time.

In another preferred embodiment, the cool regeneration gas is first introduced to the inlet of the first adsorbent zone at a temperature of between about 70° F. and 130° F. to effect the initial cooling and movement of the thermal pulse into the $CO_2$ adsorbent zone. The cool regeneration gas is subsequently introduced at a temperature of between about 40° F. and 70° F., thus reducing the energy consumed in the chiller.

This process may also be employed with feed gas pressures from appoximately atmospheric to 3,000 psia or above at feed gas temperatures from about 40° to 130° F. or above.

It is thus apparent from the description of the invention and the example that regeneration of molecular sieve adsorbents used for the removal of water and carbon dioxide contaminants from a feed gas stream may be accomplished in a manner to obtain short cycle periods, reduced energy consumption and lowered capital investment. Variations will be apparent to those skilled in the art without departing from the spirit or the scope of this invention.

What is claimed is:

1. A method for the regeneration of molecular sieve adsorbents used in the adsorption of water and carbon dioxide contaminants from a feed gas stream passed sequentially through first and second adsorbent zones containing molecular sieve wherein the water is adsorbed in the first adsorbent zone and the carbon dioxide is adsorbed in the second adsorbent zone, which comprises:

(a) regenerating the first adsorbent zone by introducing a heated regeneration gas stream intermediate the first and second adsorbent zones, and passing the heated regeneration gas through the first adsorbent zone in a direction countercurrent to the flow of the feed gas stream therethrough; and subsequently (b) cooling the first adsorbent zone and regenerating the second adsorbent zone by passing cooled regeneration gas sequentially through the first and second adsorbent zones in a direction cocurrent to the flow of the feed gas stream therethrough.

2. The method of claim 1 wherein the heated regeneration gas is introduced at a temperature of between about 450° F. and 700° F. until the temperature of the heated regeneration gas exiting the first adsorbent zone rises to a temperature of from about 250° F. to about 350° F. and the cooled regeneration gas is then introduced at a temperature from about 40° F. to about 130° F.

3. The method of claim 1 wherein the cooled regeneration gas is first introduced at a temperature from about 70° F. to 130° F. for a first portion of the cooling step and is subsequently introduced at a temperature from about 40° F. to approximately 70° F. for the latter part of step b.

4. The method of claim 1 or 3 wherein the major component of the feed gas stream is selected from the group consisting of air, hydrogen, or methane.

5. The method of claim 1 or 3 wherein the feed gas stream comprises air and the regeneration gas comprises nitrogen.

6. A cyclic process for the separation of water and carbon dioxide contaminants from a feed gas stream by adsorption on a molecular sieve adsorbent to produce a purified gas stream and subsequent regeneration of the adsorbent which comprises:

(a) passing the feed gas stream at a pressure of from about 90 to 3000 psig and a temperature of from about 40° F. to 130° F. through first and second molecular sieve adsorbent zones, wherein substantially all of the water is adsorbed in the first adsorbent zone and the carbon dioxide is adsorbed in the second adsorbent zone;

(b) discontinuing the flow of the feed gas stream to the first and second adsorbent zones;

(c) depressurizing the adsorbent zones through the inlet to a regeneration pressure of between about 14.7 and 100 psig;

(d) regenerating the first adsorbent zone by introducing heated regeneration gas at a temperature between about 450° F. and 700° F. intermediate the first and second adsorbent zones, and passing the heated regeneration gas through the first adsorbent zone in a direction countercurrent to the flow of the feed gas stream; and (e) cooling the first adsorbent zone and requenching and cooling the second adsorbent zone by passing cool regeneration gas at a temperature between about 40° F. and 130° F. sequentially through the first and second adsorbent zones in a direction cocurrent to the flow of the feed gas stream.

7. The process of claim 6 wherein the feed gas stream comprises air.

* * * * *